(12) United States Patent
Kiss et al.

(10) Patent No.: US 9,169,170 B2
(45) Date of Patent: Oct. 27, 2015

(54) HYDROALKYLATING PROCESS

(71) Applicant: ExxonMobil Chemical Patents Inc., Baytown, TX (US)

(72) Inventors: Gabor Kiss, Hampton, NJ (US); Keith H. Kuechler, Friendswood, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 0 days.

(21) Appl. No.: 14/477,243

(22) Filed: Sep. 4, 2014

(65) Prior Publication Data

US 2015/0094494 A1 Apr. 2, 2015

Related U.S. Application Data

(60) Provisional application No. 61/885,336, filed on Jan. 16, 2014.

(30) Foreign Application Priority Data

Jan. 16, 2014 (EP) .................................... 14151420

(51) Int. Cl.
| | |
|---|---|
| C07C 45/43 | (2006.01) |
| C07C 37/08 | (2006.01) |
| C07C 2/66 | (2006.01) |
| C07C 2/74 | (2006.01) |
| C07C 45/53 | (2006.01) |
| C07C 407/00 | (2006.01) |
| C07C 5/03 | (2006.01) |

(52) U.S. Cl.
CPC ... *C07C 2/74* (2013.01); *C07C 5/03* (2013.01); *C07C 37/08* (2013.01); *C07C 45/53* (2013.01); *C07C 407/00* (2013.01); *C07C 2101/14* (2013.01); *C07C 2521/04* (2013.01); *C07C 2521/06* (2013.01); *C07C 2521/08* (2013.01); *C07C 2523/42* (2013.01); *C07C 2523/44* (2013.01); *C07C 2523/46* (2013.01); *C07C 2523/755* (2013.01); *C07C 2529/70* (2013.01); *C07C 2529/74* (2013.01)

(58) Field of Classification Search
CPC .............................. C07C 45/43; C07C 37/08
USPC ........... 568/376, 798, 799; 585/267, 268, 467
See application file for complete search history.

(56) References Cited

U.S. PATENT DOCUMENTS

| | | |
|---|---|---|
| 4,439,409 A | 3/1984 | Puppe et al. |
| 4,826,667 A | 5/1989 | Zones et al. |
| 4,954,325 A | 9/1990 | Rubin et al. |
| 5,236,575 A | 8/1993 | Bennett et al. |
| 5,250,277 A | 10/1993 | Kresge et al. |
| 5,362,697 A | 11/1994 | Fung et al. |
| 6,014,018 A | 1/2000 | Wu et al. |
| 6,037,513 A | 3/2000 | Chang et al. |
| 6,077,498 A | 6/2000 | Diaz Cabanas et al. |
| 6,730,625 B1 | 5/2004 | Chang et al. |
| 6,756,030 B1 | 6/2004 | Rohde et al. |
| 7,579,511 B1 | 8/2009 | Dakka et al. |
| 2012/0277472 A1* | 11/2012 | Dakka et al. .................. 568/376 |

FOREIGN PATENT DOCUMENTS

| | | |
|---|---|---|
| EP | 0 293 032 | 11/1988 |
| WO | WO97/17290 | 5/1997 |
| WO | WO2009/128984 | 10/2009 |
| WO | WO2009/131769 | 10/2009 |
| WO | WO2011/100013 | 8/2011 |
| WO | WO2012/036822 | 3/2012 |
| WO | WO2012/050751 | 4/2012 |
| WO | WO2013/058882 | 4/2013 |
| WO | WO2013/119407 | 8/2013 |
| WO | WO2013/165662 | 11/2013 |
| WO | WO2014/018251 | 1/2014 |
| WO | WO2014/074248 | 5/2014 |
| WO | WO2014/093177 | 6/2014 |

OTHER PUBLICATIONS

PCT/US2014/021235, filed Mar. 6, 2014 entitled "Process for Making Alkylated Aromatic Compound".
PCT/US2014/021280, filed Mar. 6, 2014 entitled "Process for Making Alkylated Aromatic Compound".
PCT/US2014/041410, filed Jun. 6, 2014 entitled "Process for Concentrating a Mixture Containing Organic Hydroperoxide".

* cited by examiner

*Primary Examiner* — Sikarl Witherspoon
(74) *Attorney, Agent, or Firm* — Siwen Chen; Stephen A. Baehl

(57) ABSTRACT

An alkylating process such as hydroalkylating process comprising feeding a gas material and a liquid material into the reactor, distributing the liquid material to the upper surface of a bed of a catalyst substantially uniformly. The substantial uniform distribution of the liquid material to the upper surface allows for substantially uniform distribution of liquid reaction medium in the bed, thereby preventing hot spot and undesirable continuous liquid zone, both of which can cause the production of undesired by-products. The invention is particularly useful for the hydroalkylation reaction of benzene in making cyclohexylbenzene, which can be used for making cyclohexanone and phenol.

24 Claims, 1 Drawing Sheet

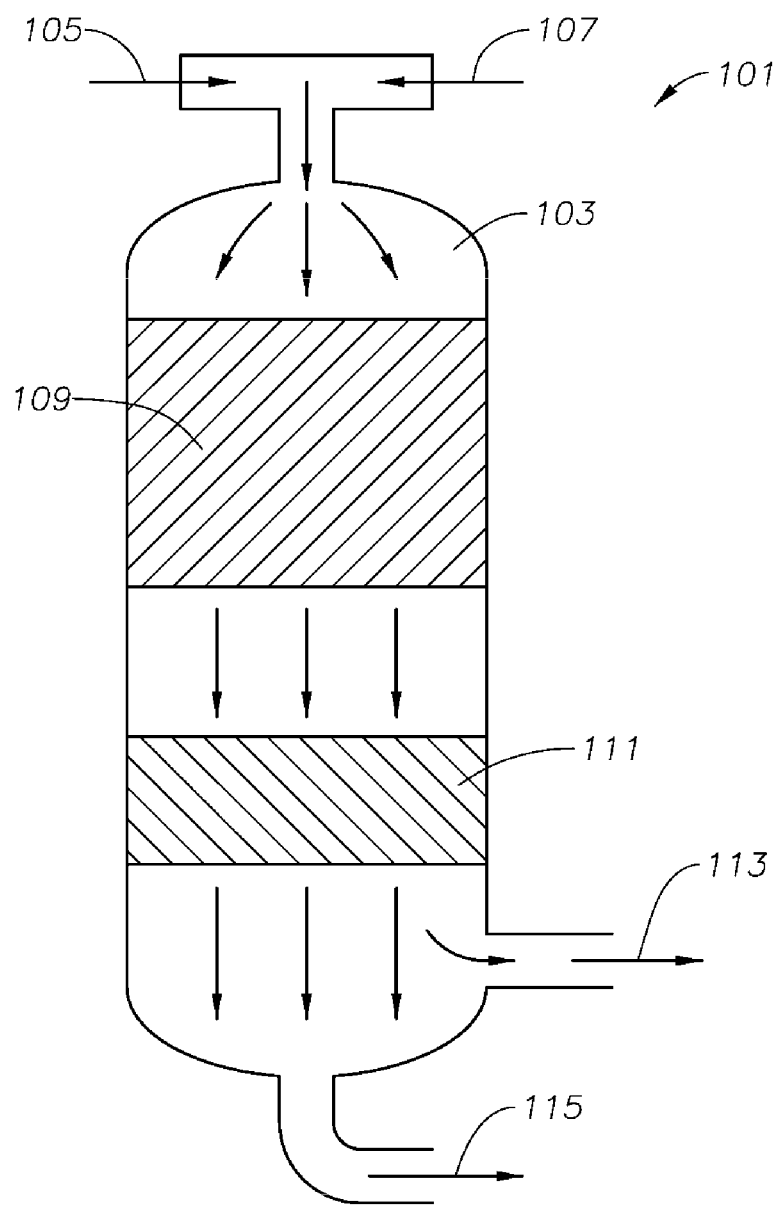

HYDROALKYLATING PROCESS

PRIORITY CLAIM

This application claims priority to U.S. Provisional Application Ser. No. 61/885,336 filed Oct. 1, 2013, and European Application No. 14151420.8 filed Jan. 16, 2014, the disclosures of which are fully incorporated herein by their reference.

FIELD

The present invention relates to a process for hydroalkylating an aromatic compound. In particular, the present invention relates to a process for hydroalkylating benzene for making cyclohexylbenzene. The present invention is useful, e.g., in making phenol and cyclohexanone via the route of benzene hydroalkylation.

BACKGROUND

Phenol and cyclohexanone are important materials in the chemical industry and are useful in, for example, the production of phenolic resins, bisphenol A, $\epsilon$-caprolactam, adipic acid, and plasticizers.

Currently, a common route for the production of phenol is the Hock process. This is a three-step process in which the first step involves alkylation of benzene with propylene to produce cumene, followed by oxidation of cumene to the corresponding hydroperoxide, and then cleavage of the hydroperoxide to produce equimolar amounts of phenol and acetone. However, the world demand for phenol is growing more rapidly than that for acetone. In addition, the cost of propylene feed is generally high.

Thus, a process that uses higher alkenes instead of propylene as feed and coproduces higher ketones, such as cyclohexanone, rather than acetone may be an attractive alternative route to the production of phenols. There is also a growing demand for cyclohexanone.

It is known from, e.g., U.S. Pat. No. 6,037,513 that cyclohexylbenzene can be produced by contacting benzene with hydrogen in the presence of a bifunctional catalyst comprising a molecular sieve of the MCM-22 type and at least one hydrogenation metal selected from Pd, Ru, Ni, Co, and mixtures thereof. This reference also discloses that the resultant cyclohexylbenzene can be oxidized to the corresponding hydroperoxide which is then decomposed to the desired phenol and cyclohexanone co-product.

It has been found that in hydroalkylation process of an aromatic compound such as benzene, a non-negligible amount of olefins, especially phenylcyclohexene, is produced. Phenylcyclohexene is difficult to separate from cyclohexylbenzene due to their close boiling. If left unconverted to cyclohexylbenzene, phenylcyclohexene will be eventually converted into undesirable by-products, which will be discarded and cause a yield loss. Thus, WO 2011/100013 A1 teaches combining the phenylcyclohexene-containing hydroalkylation stream with other phenylcyclohexene-containing recycle stream(s), and subjecting the combined stream to hydrogenation to convert phenylcyclohexene into cyclohexylbenzene. This process would require a dedicated, separate and stand-alone hydrogenation reactor for this purpose.

Therefore, there is a need for an improved hydroalkylation process.

SUMMARY

The present disclosure relates to a hydroalkylation process in which olefins produced in the hydroalkylation process, such as phenylcyclohexene produced in benzene hydroalkylation, is subjected to hydrogenation in the same hydroalkylation reactor before exiting the hydroalkylation reactor by contacting the hydroalkylation reaction mixture with a hydrogenation catalyst. Because the present invention only requires the placement of a layer of hydrogenation catalyst on the route of the hydroalkylation reaction mixture to the exit of the hydroalkylation reactor, it reduces or removes the phenylcyclohexene in the hydroalkylation effluent without the complexity and high cost of using a stand-alone hydrogenation reactor proposed in WO2011/100013 A1. In the process of the present disclosure, the same reaction conditions such as temperature and pressure applicable to the hydroalkylation reaction step in the hydroalkylation reactor can be advantageously applied to the subsequent hydrogenation step.

Thus, a first aspect of the present disclosure relates to a hydroalkylation process, the process comprising:

(I) supplying hydrogen and an aromatic compound into a hydroalkylation reactor;

(II) contacting the hydrogen and the aromatic compound with a hydroalkylation catalyst comprising a first hydrogenation metal component and an alkylation component in a first reaction zone in the hydroalkylation reactor to obtain a first reaction mixture comprising hydrogen, an alkylated aromatic compound and an olefin; and (III) contacting the first reaction mixture with a hydrogenation catalyst comprising a second hydrogenation metal component and essentially free of an alkylation component in a second reaction zone in the hydroalkylation reactor to obtain a second reaction mixture.

A second aspect of the present disclosure relates to a process for making phenol and/or cyclohexanone, the process comprising:

(A) producing cyclohexylbenzene by:
  (I) supplying hydrogen and benzene into a hydroalkylation reactor;
  (II) contacting the hydrogen and benzene with a hydroalkylation catalyst comprising a first hydrogenation metal component and an alkylation component in a first reaction zone in the reactor to obtain a first reaction mixture comprising hydrogen, cyclohexylbenzene and phenylcyclohexene; and
  (III) contacting the first reaction mixture with a hydrogenation catalyst comprising a second hydrogenation metal component and essentially free of an alkylation component in a second reaction zone in the hydroalkylation reactor to obtain a second reaction mixture comprising cyclohexylbenzene;

(B) oxidizing at least a portion of the cyclohexylbenzene in the second reaction mixture to obtain an oxidation product comprising cyclohexylbenzene hydroperoxide; and (C) subjecting at least a portion of the cyclohexylbenzene hydroperoxide in the oxidation product to cleavage to obtain a cleavage product comprising phenol and cyclohexanone.

A third aspect of the present disclosure relates to a hydroalkylation reactor comprising a vessel comprising:

at least one upper port through which $H_2$ and an aromatic compound can be fed into the vessel;

a bed of a hydroalkylation catalyst in proximity to but below the at least one upper port comprising a first hydrogenation metal component and an alkylation component in a first reaction zone;

a bed of a hydrogenation catalyst comprising a second hydrogenation metal component and essentially free of an alkylation component in a second reaction zone below the first reaction zone; and at least one lower port below the bed of the hydrogenation catalyst through which the hydroalkylation effluent can exit the reactor.

BRIEF DESCRIPTION OF THE DRAWINGS

FIG. 1 is a schematic illustration of a hydroalkylation process in operation according to an embodiment of the present disclosure.

DETAILED DESCRIPTION

In the present disclosure, a process is described as comprising at least one "step." It should be understood that each step is an action or operation that may be conducted once or multiple times in the process, in a continuous or discontinuous fashion. Unless specified to the contrary or the context clearly indicates otherwise, the steps in a process may be conducted sequentially in the order as they are listed, with or without overlapping with one or more other step(s), or in any other order, as the case may be. In addition, two or more or even all steps may be conducted simultaneously with regard to the same or different batch of material. For example, in a continuous process, while a first step in a process is being conducted with respect to a raw material just fed into the beginning of the process, a second step may be conducted simultaneously with respect to an intermediate material resulting from treating the raw materials fed into the process at an earlier time in the first step. Preferably, steps are performed in the order listed.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal" include embodiments where one, two or more different types of the hydrogenation metal(s) are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

As used herein, the generic term "dicylcohexylbenzene" includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in singular form, means mono substituted cyclohexylbenzene.

As used herein, the generic term "phenylcyclohexene" includes, in the aggregate, 2-phenyl-1-cyclohexene, 3-phenyl-1-cyclohexene, and 4-phenyl-1-cyclohexene, unless clearly specified to mean only one or two thereof.

The term "MCM-22 type material" (or "material of the MCM-22 type," "molecular sieve of the MCM-22 type," or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve is selected from (a) MCM-49; (b) MCM-56; and (c) isotypes of MCM-49 and MCM-56, such as ITQ-2.

A hydroalkylation process according to the present disclosure may involve a gaseous phase comprising hydrogen, a liquid phase comprising an aromatic compound subjected to hydroalkylkation, and a hydroalkylation reaction taking place in the presence of a solid phase catalyst.

In the process of the present disclosure, the aromatic compound supplied to the hydroalkylation reactor may have the following general formula (F-I):

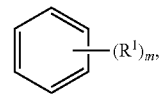

(F-I)

where:

$R^1$, the same or different at each occurrence, each independently represents a substituted or unsubstituted linear, branched acyclic, or cyclic alkyl or alkenyl group having from 1 to 20 carbon atoms (such as 1 to 10, or 1 to 5 carbon atoms); and m is an integer from 0 to 5.

Non-limiting examples of such aromatic compounds include: benzene, toluene, ethylbenzene, n-propylbenzene, cumene, n-butylbenzene, 2-phenylbutane, o-xylene, m-xylene, p-xylene, o-methylethylbenzene, m-methylethylbenzene, p-methylethylbenzene, and the like.

A desired product in the reaction effluent of the alkylation process can be an alkylated aromatic compound represented by the following general formula (F-II):

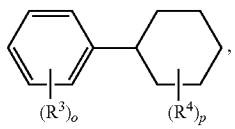

(F-II)

where:

R³ and R⁴, the same or different at each occurrence, each independently represents a substituted or unsubstituted linear, branched acyclic, or cyclic alkyl or alkenyl having from 1 to 20 carbon atoms (such as from 1 to 10, or from 1 to 5); and o and p are independently integers from 0 to 5.

Non-limiting examples of compounds having formula (F-II) include:

cyclohexylbenzene;
dicyclohexylbenzene;
tricyclohexylbenzene;
methylcyclohexyltoluene;
methylcyclohexyl-ethylbenzene;
ethylcyclohexyl-ethylbenzene;
propylcyclohexyl-propylbenzene;
butylcyclohexyl-butylbenzene;
dimethylcyclohexyl-dimethylbenzene;
diethylcyclohexyl-diethylbenzene;
trimethylcyclohexyl-trimethylbenzene;
isopropylcyclohexylcumene;
methylethylcyclohexyl-methylethylbenzene; and
combinations and mixtures of at least two thereof.

However, in the hydroalkylation of an aromatic compound of formula (F-I) to make an alkylated aromatic compound of formula (F-II), various amounts of olefin having the following general formula (F-III), (F-IV), and (F-V) is produced depending on the reaction conditions:

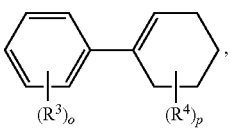

(F-III)

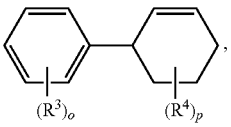

(F-IV)

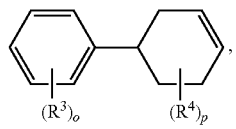

(F-V)

where R³, R⁴, o, and p have the same meaning as in formula (F-II). The olefins of formulae (F-III), (F-IV), and (F-V) have similar boiling points to that of the desired product having formula (F-II), and therefore are difficult to separate by distillation. If fed to the next process step together with the formula (F-II) product, these olefins can undergo undesired chemical reactions, resulting in yield loss and contamination of products of the next step(s). As such, there is a need to convert these formulae (F-III), (F-IV), and (F-V) olefins to the product of formula (F-II), which can be accomplished, e.g., in a separate hydrogenation reactor where the (F-III), (F-IV), and (F-V) olefins react with $H_2$ in the presence of a hydrogenation catalyst under hydrogenation conditions.

In the hydroalkylation process of benzene with hydrogen to produce cyclohexylbenzene, a $H_2$-containing gas feed and a liquid benzene-containing liquid feed may be charged into the hydroalkylation reactor, where the following reactions, among others, may take place on the surface of a bi-functional hydroalkylation catalyst comprising a hydrogenation metal component such as Pd and a solid acid component such as a molecular sieve of the MCM-22 type:

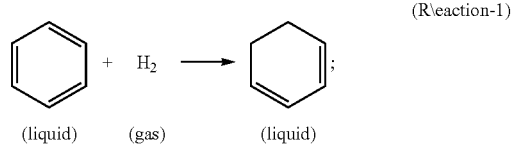

(R\eaction-1)

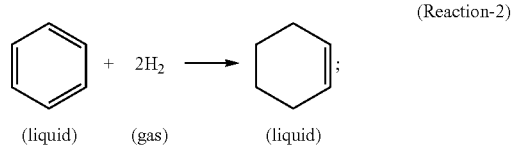

(Reaction-2)

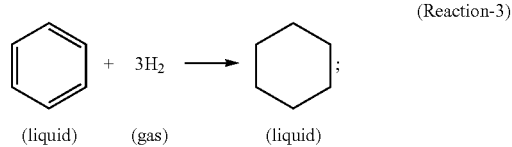

(Reaction-3)

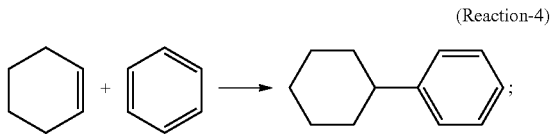

(Reaction-4)

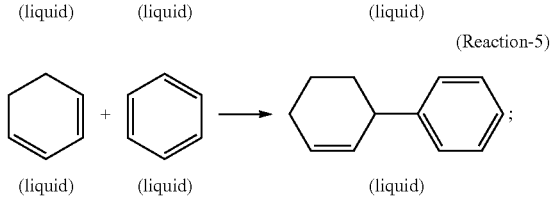

(Reaction-5)

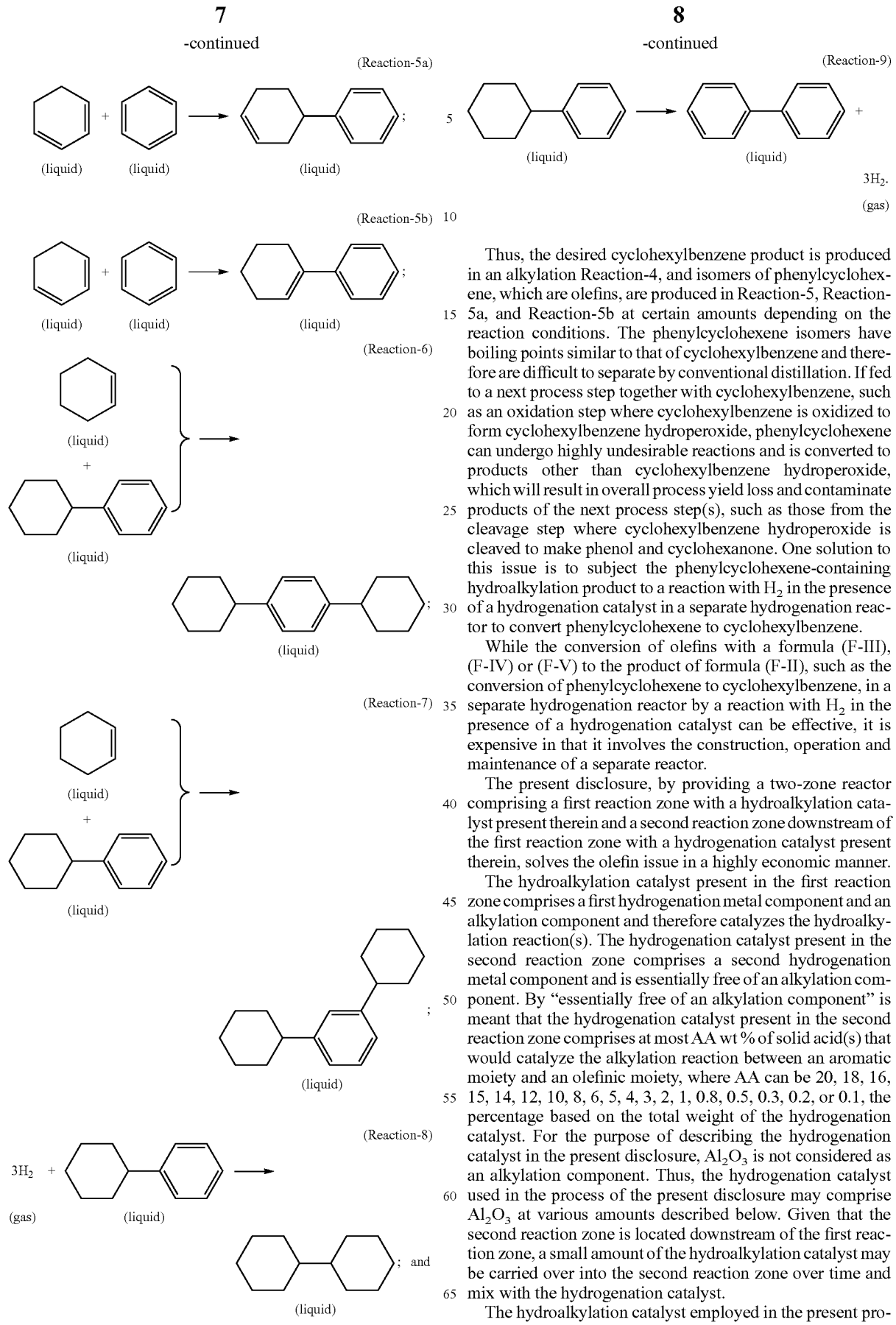

Thus, the desired cyclohexylbenzene product is produced in an alkylation Reaction-4, and isomers of phenylcyclohexene, which are olefins, are produced in Reaction-5, Reaction-5a, and Reaction-5b at certain amounts depending on the reaction conditions. The phenylcyclohexene isomers have boiling points similar to that of cyclohexylbenzene and therefore are difficult to separate by conventional distillation. If fed to a next process step together with cyclohexylbenzene, such as an oxidation step where cyclohexylbenzene is oxidized to form cyclohexylbenzene hydroperoxide, phenylcyclohexene can undergo highly undesirable reactions and is converted to products other than cyclohexylbenzene hydroperoxide, which will result in overall process yield loss and contaminate products of the next process step(s), such as those from the cleavage step where cyclohexylbenzene hydroperoxide is cleaved to make phenol and cyclohexanone. One solution to this issue is to subject the phenylcyclohexene-containing hydroalkylation product to a reaction with $H_2$ in the presence of a hydrogenation catalyst in a separate hydrogenation reactor to convert phenylcyclohexene to cyclohexylbenzene.

While the conversion of olefins with a formula (F-III), (F-IV) or (F-V) to the product of formula (F-II), such as the conversion of phenylcyclohexene to cyclohexylbenzene, in a separate hydrogenation reactor by a reaction with $H_2$ in the presence of a hydrogenation catalyst can be effective, it is expensive in that it involves the construction, operation and maintenance of a separate reactor.

The present disclosure, by providing a two-zone reactor comprising a first reaction zone with a hydroalkylation catalyst present therein and a second reaction zone downstream of the first reaction zone with a hydrogenation catalyst present therein, solves the olefin issue in a highly economic manner.

The hydroalkylation catalyst present in the first reaction zone comprises a first hydrogenation metal component and an alkylation component and therefore catalyzes the hydroalkylation reaction(s). The hydrogenation catalyst present in the second reaction zone comprises a second hydrogenation metal component and is essentially free of an alkylation component. By "essentially free of an alkylation component" is meant that the hydrogenation catalyst present in the second reaction zone comprises at most AA wt % of solid acid(s) that would catalyze the alkylation reaction between an aromatic moiety and an olefinic moiety, where AA can be 20, 18, 16, 15, 14, 12, 10, 8, 6, 5, 4, 3, 2, 1, 0.8, 0.5, 0.3, 0.2, or 0.1, the percentage based on the total weight of the hydrogenation catalyst. For the purpose of describing the hydrogenation catalyst in the present disclosure, $Al_2O_3$ is not considered as an alkylation component. Thus, the hydrogenation catalyst used in the process of the present disclosure may comprise $Al_2O_3$ at various amounts described below. Given that the second reaction zone is located downstream of the first reaction zone, a small amount of the hydroalkylation catalyst may be carried over into the second reaction zone over time and mix with the hydrogenation catalyst.

The hydroalkylation catalyst employed in the present process is a bifunctional catalyst comprising an alkylation component such as a solid acid and a first hydrogenation metal component, optionally a first inorganic oxide support component, and optionally a binder.

Suitable solid acid for the alkylation component include mixed metal oxides, for example, tungstated zirconia, and molecular sieves, for example, zeolite beta, zeolite X, zeolite Y, mordenite and zeolites of the MWW framework type (see "Atlas of Zeolite Framework Types", Fifth edition, 2001). As examples of molecular sieves of the MWW framework type, MCM-22 type molecular sieves are particularly advantageous. Desirably, the molecular sieve of the MWW framework type is MCM-22 or MCM-49.

Any known hydrogenation metal component can be employed as the first hydrogenation component in the hydroalkylation catalyst. Particularly advantageous examples include Pd, Pt, Ru, Fe, Rh, Os, Ir, Ni, Zn, Sn, and Co, with Pd and Pt being especially desirable. The amount of hydrogenation metal component present in the hydroalkylation catalyst may be in a range from $Chma1$ wt % to $Chma2$ wt %, based on the total weight of the hydroalkylation catalyst, where $Chma1$ and $Chma2$ can be, independently, 0.01, 0.02, 0.03, 0.04, 0.05, 0.06, 0.07, 0.08, 0.09, 0.10, 0.12, 0.15, 0.20, 0.25, 0.30, 0.35, 0.40, 0.45, 0.50, 0.60, 0.70, 0.80, 0.90, 1.0, 2.0, 3.0, 4.0, 5.0, 6.0, 7.0, 8.0, 9.0, or even 10.0, as long as $Chma1<Chma2$. Where the solid acid component of the catalyst is an aluminosilicate molecular sieve, the molar ratio of the aluminum in the molecular sieve to the first hydrogenation metal may be in a range from 1.5 to 1500, for example in a range from 30 to 750, or in a range from 75 to 750, such as in a range from 30 to 300.

The first hydrogenation metal may be directly supported on the alkylation component by, for example, impregnation or ion exchange, or can be supported on the first inorganic oxide support component, or both. At least $A1$ wt % of the first hydrogenation metal component can be supported on the first inorganic oxide support component separate from but composited with the alkylation component, where the percentage is based on the total weight of the hydroalkylation catalyst, and $A1$ can be: 50, 55, 60, 75, 80, 85, 90, 95, 98, 99, or even 99.5. By supporting a majority of the first hydrogenation metal component on the first inorganic oxide support component, the activity of the catalyst and its selectivity to cyclohexylbenzene, dicyclohexylbenzene, and tricyclohexylbenzene in the hydroalkylation reaction are increased as compared with an equivalent catalyst in which the first hydrogenation metal component is supported directly on the solid acid component.

The first inorganic oxide support component contained in such a composite hydroalkylation catalyst is not narrowly defined provided it is stable and inert under the conditions of the hydroalkylation reaction. Suitable inorganic oxides include oxides of elements in Groups 2, 3, 4, 5, 13, and 14 of the Periodic Table of Elements. Examples of suitable and widely available inorganic oxides include, for example, alumina, silica, silica-alumina, titania, zirconia, and combinations and mixtures thereof. As used herein, the numbering scheme for the Periodic Table Groups is as disclosed in Chemical and Engineering News, 63(5), 27 (1985).

Loading the first hydrogenation metal component on the first inorganic oxide support component can be conveniently effected by impregnation of the first inorganic oxide support component with a solution of a salt of the desired metal, which can be followed by compositing with the alkylation component such as solid acid. For example, the catalyst composite may be produced by co-pelletization, in which a mixture of the alkylation component and the metal-containing first inorganic oxide support component is formed into pellets at high pressure (e.g., from 350 kPa to 350,000 kPa), or by co-extrusion, in which a slurry of the alkylation component and the metal-containing first inorganic oxide support component, optionally together with a separate binder, which can be organic or inorganic, are forced through a die. Examples of inorganic binder materials are described below. If necessary, additional amount of the first hydrogenation metal component can be subsequently deposited on the resultant catalyst composite.

Alternatively, the alkylation component is first extruded with the inorganic oxide component, and then the first hydrogenation metal is impregnated into the extrudate. In this case, the impregnation conditions can be adjusted such that the first hydrogenation metal is preferentially associated with the oxide component of the extrudate.

The hydroalkylation catalyst may further comprise an optional inorganic binder, non-limiting examples of which include clay, silica and/or metal oxides. Naturally occurring clays which can be used as a binder include those of the montmorillonite and kaolin families, which families include the subbentonites and the kaolins commonly known as Dixie, McNamee, Ga., and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia. The binder mechanically connects catalytically active particles comprising the first hydrogenation metal, the solid acid, and optionally an first inorganic oxide support component into a larger body, such as a pellet, a cylinder, a pill, and the like, which can be conveniently loaded into a hydroalkylation reactor.

Immediately after the incorporation of the first hydrogenation metal component, the alkylation component, optionally the first inorganic oxide support component, and optionally the binder, a catalyst precursor of the hydroalkylation catalyst is formed. The first hydrogenation metal is normally in an oxidized form in the precursor and therefore, before being employed in a hydroalkylation process, the resultant catalyst precursor is desirably activated to convert at least some of the first hydrogenation metal to its zero-valent elemental state. The activation process can be conducted by heating the catalyst precursor in the presence of hydrogen in, e.g., the same reactor as that used for the subsequent hydroalkylation step. However, if desired, the activation may be conducted in one or more separate reactors and the activated catalyst is subsequently transferred to the hydroalkylation reactor. Activation of the hydroalkylation catalyst can be effected using the processes described in co-pending, co-assigned: PCT application No. PCT/US2013/049720, filed on Jul. 9, 2013 and entitled "Activation and Use of Hydroalkylation Catalysts;" U.S. Provisional Application Ser. No. 61/712,980, filed on Oct. 12, 2012 and entitled "Activation and Use of Hydroalkylation Catalysts;" and WO2012/050751, the contents of all of which are incorporated herein by reference.

The hydrogenation catalyst comprises a second hydrogenation metal component, which may be the same as or different from the first hydrogenation metal component contained in the hydroalkylation catalyst described above. Thus, particularly advantageous non-limiting examples of the second hydrogenation metal include Pd, Pt, Ru, Fe, Rh, Os, Ir, Ni, Zn, Sn, and Co, with Pd and Pt being especially desirable. The amount of the second hydrogenation metal component present in the hydroalkylation catalyst is in a range from, based on the total weight of the hydrogenation catalyst, Chmb1 wt % to Chmb2 wt %, based on the total weight of the hydroalkylation catalyst, where Chmb1 and Chmb2 can be, independently, 0.01, 0.02, 0.03, 0.04, 0.05, 0.06, 0.07, 0.08, 0.09, 0.10, 0.12, 0.15, 0.20, 0.25, 0.30, 0.35, 0.40, 0.45, 0.50, 0.60, 0.70, 0.80, 0.90, 1.0, 2.0, 3.0, 4.0, 5.0, 6.0, 7.0, 8.0, 9.0, or even 10.0, as long as Chmb1<Chmb2.

In addition to the second hydrogenation metal component, the hydrogenation catalyst comprises a second inorganic oxide support, which may be the same as or different from the first inorganic oxide support component contained in the hydrogenation catalyst. Non-limiting examples of the second inorganic oxide support includes oxides of elements in Groups 2, 3, 4, 5, 13, and 14 of the Periodic Table of Elements, such as alumina, silica, silica-alumina, titania, zirconia, and combinations and mixtures thereof. Desirably a great majority of the second hydrogenation metal is supported on the surface of the second inorganic oxide support.

The hydrogenation catalyst may further optionally contain an inorganic binder that is the same or different from the inorganic binder that may be contained in the hydrogenation catalyst described above. The inorganic binder binds small catalytically active particles together to form larger shaped hydrogenation catalyst, such as pellets, pills, cylinders, and the like.

The hydrogenation catalyst can be made by a process similar to the process for making the hydroalkylation catalyst described above, expect that no alkylation component is included into the starting materials. The hydrogenation catalyst may be activated by a process similar to the activation process for the hydroalkylation catalyst described above.

Examples of the hydrogenation catalyst and processes for making and activating them are provided in co-pending, co-assigned International Application Publication No. WO2011/100013; and International Application No. PCT/US2013/035920 filed on Apr. 10, 2013 and entitled "Hydrogenation Process," the contents of both of which are incorporated herein by reference in their entirety.

The hydroalkylation catalyst is located in the first reaction zone of the hydroalkylation reactor. Thus, the feed materials supplied into the hydroalkylation reactor, including the aromatic compound such as benzene and hydrogen, are mixed and allowed to contact the hydroalkylation catalyst. Desirably, the feed materials are supplied into the hydroalkylation reactor from the top and then flows downward through a bed of the hydroalkylation catalyst due to gravity and pressure gradient. On contacting the first hydrogenation metal component and alkylation component, the aromatic compound and hydrogen react to produce a first reaction mixture comprising hydrogen, an alkylated aromatic compound such as cyclohexylbenzene in the case of benzene hydroalkylation, and an olefin such as phenylcyclohexene.

The first reaction mixture then travels to the downstream second reaction zone of the hydroalkylation reactor, which is located below the first reaction zone if the aromatic compound and hydrogen feed(s) are supplied from the top of the hydroalkylation reactor, where the hydrogenation catalyst is located. On contacting the second hydrogenation metal component in the hydrogenation catalyst, the olefin and hydrogen contained in the first reaction mixture react with each other to convert the olefin to an alkylated aromatic compound, which may form a portion of the desirable product, and obtain a second reaction mixture exiting the hydroalkylation reactor. The second reaction mixture typically contains some residual hydrogen and the aromatic compound from the feed, and the desired alkylated aromatic compound. The olefins) contained in the first reaction mixture, which would otherwise form a portion of the effluent exiting the hydroalkylation reactor if the reactor does not contain the second reaction zone, is reduced to a negligible level in the second reaction mixture, for example, at a concentration of at most BB ppm by weight of the second reaction mixture, where BB can be 100, 90, 80, 70, 60, 50, 40, 30, 20, 10, 8, 6, 5, 4, 3, 2, or even 1.

It has been found that the molar ratio of hydrogen gas to the aromatic compound fed into the reactor partly determines the extent to which the above desired and undesired reactions take place on the catalyst. For example, in the case of hydroalkylation of benzene, where there is a substantial oversupply of $H_2$, more cyclohexane via Reaction-3 and bicyclohexylbenzene via Reaction-6 and Reaction-7 may be produced; and in the case of a substantial oversupply of benzene, more biphenyls via Reaction-9 may be produced. In a hydroalkylation reaction where the target product is cyclohexylbenzene, all by-products cyclohexane, biphenyl, and bicyclohexane are undesired and should be minimized. Therefore, the molar ratio of $H_2$ to benzene is desired to be within a given range in the feed materials, such as from RM1 to RM2, where RM1 can be 0.01, 0.05, 0.10, 0.15, 0.20, 0.25, 0.30, 0.35, 0.40, 0.45, 0.50, 0.60, 0.80, 1.00, and RM2 can be 15.0, 10.0, 8.0, 6.0, 4.0, 2.0, 1.5, 1.0, 0.90, 0.80, 0.70, 0.60, as long as RM1<RM2. Advantageously, RM1 is 0.10, and RM2 is 1.5.

It is highly desired that the aromatic compound fed into the hydroalkylation reactor is in a liquid state, while hydrogen is supplied into the hydroalkylation reactor as a stream of gas containing hydrogen gas and optionally an inert gas such as methane. The two feed materials may be combined before or immediately after entering the hydroalkylation reactor.

The process according to the present disclosure may be conducted in a fixed-bed catalyst reactor, where the catalyst particles are packed inside a column, and the gas and liquid materials are allowed to travel, e.g., in a direction from the top to bottom, in contact with the surface of the hydroalkylation catalyst particles and the hydrogenation catalyst particles, whereby the hydroalkylation and/or hydrogenation reactions take place.

In the process of the present disclosure, both hydrogen and the aromatic compound may be fed into the hydroalkylation reactor from a location above the bed of the hydroalkylation catalyst, mix together and travel through the hydroalkylation catalyst bed in an upper first reaction zone, produces a first reaction mixture, which travels downward through a second bed of hydrogenation catalyst and is converted into a second reaction mixture, and the second reaction mixture exits the hydroalkylation reactor at locations in proximity to the bottom of the bed of the hydrogenation catalyst, such as locations below the bottom of the bed of the catalyst. This down-flow configuration is particularly advantageous for carrying out gas-liquid reaction on the surface of a solid catalyst bed and can allow for a substantially uniform distribution of both liquid and gas in a horizontal cross-section of the solid catalysts. In such reactors, the liquid is first dispensed onto the upper surface of the hydroalkylation catalyst, then flows down the bed along the boundary of the catalyst particles, wet the surface of the catalyst particles in the bed along its way, and undergoes the desired reaction(s). A substantially uniform distribution of the liquid reaction media inside the bed of the catalyst is highly desired to control the amount of by-products produced inside the reactor. It was found that the distribution of the liquid fed into the reactor to the upper surface of the bed of the catalyst can significantly impact the distribution of the liquid reaction medium in the bulk of the bed of the catalyst. To achieve a substantially uniform distribution of the liquid reaction medium in the bulk, it is highly desired that the liquid fed into to the reactor is distributed substantially uniformly to the upper surface of the bed.

In the processes of the present disclosure, at least a portion of both of hydrogen and the aromatic compound may be fed into the hydroalkylation reactor are supplied to the reactor at the same horizontal level of the reactor. For example, hydrogen and the aromatic compound can be mixed and then fed into the hydroalkylation reactor together via the same port(s). Alternatively, hydrogen and the aromatic compound are fed into the reactor via different, separate ports. At least some of the ports through each of which hydrogen and/or the aromatic compound are fed into the reactor are above the upper surface of the bed of the hydroalkylation catalyst. For example, to facilitate a substantially uniform distribution of the liquid aromatic compound feed material to the upper surface of the bed of the hydroalkylation catalyst, a plurality of ports may be used above the upper surface of the hydroalkyation catalyst bed, through each of which a portion of the total liquid feed is delivered into the reactor. Generally, it is easier to achieve a substantially uniform distribution of the hydrogen gas in the space above the upper surface of the bed of the hydroalkylation catalyst than the liquid aromatic compound feed material. Nonetheless, to ensure such uniform distribution of hydrogen gas, multiple ports for feeding gas may be used above the upper surface of the bed of the hydroalkylation catalyst as well.

It has been found that, in order to achieve a substantially uniform distribution of the liquid feed material in the space immediately above the upper surface of the bed of the catalyst, a fluid distributing device may be desired between the inlet of the liquid and the upper surface of the bed of the catalyst. Such fluid distributing device receives at least a portion of the liquid material fed into the reactor through the inlet(s), redirects the flow thereof in multiple horizontal directions, and eventually delivers the liquid into the space above the upper surface of the bed in the form of liquid droplets. Detailed description of fluid distributing devices suitable for the process of the present disclosure can be found in co-pending, co-assigned U.S. provisional patent application Ser. No. 61/736,581, filed on Dec. 13, 2012 and entitled "Alkylating Process," the content of which is incorporated herein by reference in its entirety.

The second reaction mixture may exit the hydroalkylation reaction in a single stream comprising both gas and liquid, or in multiple streams, with one more streams comprising primarily gas, and one or more streams comprising primarily liquid.

FIG. 1 schematically illustrates a hydroalkylation process 101 according to one embodiment of the present disclosure. A liquid aromatic compound (e.g., benzene) stream 105 and a $H_2$ gas stream 107 are combined and then fed into the hydroalkylation reactor 103 from a top port. The gas/liquid mixture is then distributed to the top surface of a bed of a hydroalkylation catalyst comprising MCM-49 molecular sieve, Pd and $Al_2O_3$. As a result of gravity and pressure gradient, the reaction medium travels downward through the hydroalkylation catalyst bed 109. On contacting the surface of the hydroalkylation catalyst particles, a series of reactions occur and a first reaction mixture comprising an alkylated compound (e.g., cyclohexylbenzene), olefin (e.g., phenylcyclohexene), residual $H_2$ and residual of the aromatic compound exits the bottom of the hydroalkylation bed 109. The first reaction mixture travels further downward and through a bed of hydrogenation catalyst 111 comprising Pd and $SiO_2$. On contacting the surface of the particles of the hydrogenation catalyst, the olefin contained in the first reaction mixture reacts with hydrogen, and is converted into, e.g., the target alkylated aromatic compound. A second reaction mixture comprising the alkylated aromatic compound (e.g., cyclohexylbenzene), residual of the aromatic compound, and residual $H_2$ exits the bottom of the hydrogenation catalyst bed 111, and is subsequently divided into an upper stream 113 comprising $H_2$ and a lower stream 115 essentially free of $H_2$, which exit the hydroalkylation reactor 103 through ports in proximity to the bottom of the reactor.

The present invention can be advantageously employed in the process for making phenol and/or cyclohexanone via benzene hydroalkylation. Detailed description of the process is provided as follows.

Production of Cyclohexylbenzene

In the integrated process for producing phenol and cyclohexanone from benzene, the benzene is initially converted to cyclohexylbenzene by any conventional technique, including alkylation of benzene with cyclohexene in the presence of an acid catalyst, such as zeolite beta or an MCM-22 type molecular sieve, or by oxidative coupling of benzene to make biphenyl followed by hydrogenation of the biphenyl. However, in practice, the cyclohexylbenzene is desirably produced by contacting the benzene with hydrogen under hydroalkylation conditions in the presence of a hydroalkylation catalyst whereby the benzene undergoes the following Reaction-10 to produce cyclohexylbenzene (CHB):

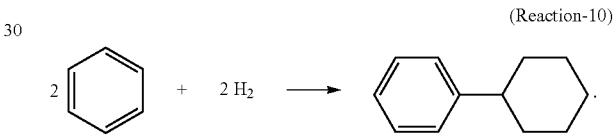

(Reaction-10)

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

The hydroalkylation process of the present disclosure described in detail above can be advantageously used for making cyclohexylbenzene essentially free of phenylcyclohexene useful in the process for making phenol and cyclohexanone.

Although the benzene hydroalkylation reaction is highly selective towards cyclohexylbenzene, the effluent from the hydroalkylation reaction may contain some dialkylated products, unreacted benzene and cyclohexane. The unreacted benzene may be recovered by distillation and recycled to the reactor. The lower effluent from the benzene distillation may be further distilled to separate the monocyclohexylbenzene product from dicyclohexylbenzene and other heavies. Depending on the quantity of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, zeolite USY, and mordenite. The transalkylation reaction is desirably conducted under at least partial liquid phase conditions, which suitably include a temperature of 100° C. to 300° C., a pressure of 800 kPa to 3500 kPa, a weight hourly space velocity of 1 hr$^{-1}$ to 10 hr$^{-1}$ on total feed, and a benzene/dicyclohexylbenzene weight ratio of 1:1 to 5:1.

Oxidation of Cyclohexylbenzene

After removal of the unreacted benzene and the polyalkylated benzenes and other heavy species, the cyclohexylbenzene produced in the hydroalkylation step is fed to an oxidizing step, which can be conducted in one or more oxidation reactor(s). Desirably, at least a portion of the cyclohexylbenzene contained in the oxidation feed is converted to cyclohexyl-1-phenyl-1-hydroperoxide, the desired hydroperoxide according to the following Reaction-11:

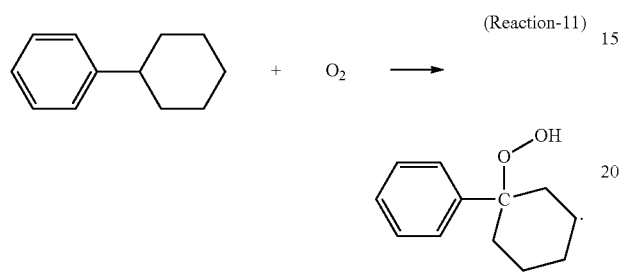

(Reaction-11)

The feed supplied to the oxidizing step may comprise cyclohexylbenzene at a concentration in a range from C1 wt % to C2 wt %, based on the total weight of the feed introduced into the oxidation reactor, where C1 and C2 can be, independently, 10, 20, 30, 40, 50, 60, 70, 80, 90, 92, 94, 95, 96, 97, 98, 99, 99.5, or even 99.9, or even higher, as long as C1<C2. In addition, the feed to the oxidizing step may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) phenylmethylcyclopentane, including one or more of 1-phenyl-1-methylcyclopentane, 1-phenyl-2-methylcyclopentane, and 1-phenyl-3-methylcyclopentane, at a total concentration in a range from 1 ppm to 2 wt %, such as from 10 ppm to 1 wt %; (iv) phenol at a concentration no greater than 1000 ppm, such as no greater than 100 ppm; and (v) olefins or alkene benzenes such as phenylcyclohexene at no greater than 1000 ppm (or no greater than 800, 600, 500, 400, 300, 200, 100, 80, 60, 50, 40, 20, 10, 8, 6, 5, 4, 2, 1 ppm), which is advantageously reduced by using the process of the present disclosure.

The oxidizing step may be accomplished by contacting an oxygen-containing gas, such as air and various derivatives of air, with the feed comprising cyclohexylbenzene. A stream of pure O$_2$, air, or other O$_2$-containing mixtures may be pumped through the cyclohexylbenzene-containing feed in an oxidation reactor such as a bubble column to effect the oxidation.

The oxidation may be conducted in the absence or presence of a catalyst. Examples of suitable oxidation catalysts include those having a structure of formula (FC-I), (FC-II), or (FC-III) below:

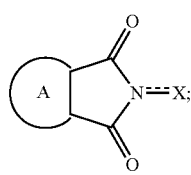

(FC-I)

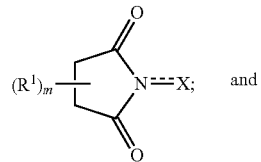

(FC-II)

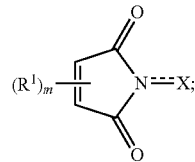

(FC-III)

where:

A represents a ring optionally comprising a nitrogen, sulfur, or oxygen in the ring structure, and optionally substituted by an alkyl group, an alkenyl group, a halogen, or a N-, S-, or O-containing group or other group;

X represents a hydrogen, an oxygen, a hydroxyl group, or a halogen;

R$^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and m is 0, 1 or 2.

Examples of particularly suitable catalysts for the oxidation step include those represented by the following formula (FC-IV):

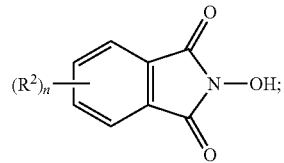

(FC-IV)

where:

R$^2$, the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

Especially suitable catalyst having the above formula (FC-IV) for the oxidation step is NHPI (N-hydroxy phthalic imide).

Non-limiting examples of suitable reaction conditions of the oxidizing step include a temperature from 70° C. to 200° C., such as 90° C. to 130° C., and a pressure of 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an O$_2$-containing gas stream (such as air) through the media. For example, the oxidation reactor may comprise a simple, largely open vessel with a distributor inlet for the oxygen-containing stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series, each operating at the same or different conditions selected to enhance the oxidation reaction of reaction media with different compositions. The oxidation reactor may be operated in a batch, semi-batch, or continuous flow manner well known to those skilled in the art.

Treatment of the Oxidation Product Before Cleavage

Desirably, the oxidation product exiting the oxidation reactor contains cyclohexyl-1-phenyl-1-hydroperoxide at a concentration in a range from Chp1 wt % to Chp2 wt %, based on the total weight of the oxidation product, where Chp1 and Chp2 can be, independently, 5, 10, 15, 20, 25, 30, 35, 40, 45, 50, 55, 60, 65, 70, 75, 80, as long as Chp1<Chp2. The oxidation product may further comprise (i) an oxidation catalyst described above; and (ii) unreacted cyclohexylbenzene at a concentration in a range from Cchb1 wt % to Cchb2 wt %, based on the total weight of the oxidation product, where Cchb1 and Cchb2 can be, independently, 20, 25, 30, 35, 40, 45, 50, 55, 60, 65, 70, 75, 80, 85, 90, 95, as long as Cchb1<Cchb2.

In addition, the oxidation product may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in feed supplied to the oxidizing step, such as cyclohexyl-2-phenyl-1-hydroperoxide, and cyclohexyl-3-phenyl-1-hydroperoxide. These undesired hydroperoxides are desirably at a total concentration of at most 5 wt %, such as at most 3 wt %, 2 wt %, 1 wt %, or even 0.1 wt %.

The oxidation product contains the oxidation catalyst, such as NHPI, and certain by-products. Thus, it may be desirable to wash the oxidation product to remove the by-products and/or the catalyst before cleavage by using an aqueous dispersion. For example, a basic aqueous dispersion, such as a solution of one or more of alkali or alkali earth carbonates, alkali or alkali earth bicarbonates, alkali or alkali earth hydroxides, ammonium hydroxide, may be used to wash the oxidation product to extract NHPI or other similar imide-based catalysts from the oxidation product. In so doing, water concentration in the oxidation product thus washed will increase.

Alternatively, to reclaim the oxidation catalyst from the oxidation product, the oxidation product may be subjected to contacting with a solid sorbent in the form of particles in a slurry or a fixed bed, such as solid alkali or alkali earth metal carbonates, alkali or alkali earth metal bicarbonates, alkali or alkali earth metal hydroxide, molecular sieves, activated carbon, and the like. After separation, the sorbent may be washed using a polar solvent, such as water, acetone, an alcohol, and the like, to reclaim the oxidation catalyst, which can be purified and recycled to the oxidation reactor.

In the process of the present disclosure, at least a portion of the cyclohexylbenzene hydroperoxide in the oxidation product is subjected to a cleavage reaction, desirably in the presence of a catalyst such as an acid, whereby it is converted into phenol and/or cyclohexanone.

At least a portion of the oxidation product may be fed into the cleavage reactor without substantial alteration of the concentration of cyclohexylbenzene hydroperoxide and/or cyclohexylbenzene therein. Thus, where the concentration of cyclohexylbenzene in the oxidation product is CCHB(op) wt % based on the total weight of the oxidation product, and the concentration of cyclohexylbenzene in the cleavage feed is CCHB(cf) wt % based on the total weight of the cleavage feed before any material other than those contained in the oxidation product is added, the following relationship may be satisfied: $(CCHB(op)-CCHB(cf))/CCHB(cf) \leq 0.05$. In such cases, the oxidation product may be flashed in a vessel at an absolute pressure in a range from Pf1 kPa to Pf2 kPa to remove a portion of water contained therein, where Pf1 and Pf2 can be, independently, 2.50, 2.67, 3.00, 3.50, 4.00, 4.50, 5.00, 5.50, 6.00, 6.50, 6.67, 7.00, 7.50, 8.00, 8.50, 9.00, 10.00, 11.00, 12.00, 13.00, 13.33, 14.00, 15.00, 16.00, 17.00, 18.00, 19.00, 20.00, 25.00, 30.00, 35.00, 40.00, 45.00, or 50.00, as long as Pf1<Pf2. Desirably, the oxidation product is flashed in a vessel, such as a flashing drum, at an absolute pressure in a range from 6.67 kPa (50 torr) to 13.33 kPa (100 torr). During the flashing step, other low boiling components that may be present in the oxidation product, such as lower acids (e.g., formic acid, acetic acid, and the like) and low boiling point hydrocarbons (e.g., benzene, cyclohexane, methylcyclopentane, and the like), may be at least partially removed along with water, resulting in a cleaner cleavage feed.

Desirably, at least a portion of the oxidation product is not fed into the cleavage reactor before the concentration of cyclohexylbenzene therein is significantly reduced, and hence, the concentration of cyclohexylbenzene hydroperoxide is significantly increased. Thus, where the concentration of cyclohexylbenzene in the oxidation product is CCHB(op) wt % based on the total weight of the oxidation product, and the concentration of cyclohexylbenzene in the cleavage feed is CCHB(cf) wt % based on the total weight of the cleavage feed before any material other than those contained in the oxidation product is added, the following relationship may be satisfied: $R1 < (CCHB(op)-CCHB(cf))/CCHB(op)) \leq R2$, where R1 and R2 are, independently, 0.05, 0.08, 0.10, 0.12, 0.14, 0.15, 0.18, 0.20, 0.25, 0.30, 0.35, 0.40, 0.45, 0.50, 0.55, 0.60, 0.70, 0.75, 0.80, 0.85, or even 0.90, as long as R1<R2. Desirably, R1=0.25, and R2=0.75. The reduction of cyclohexylbenzene concentration from the oxidation product before cleavage is particularly advantageous where liquid acid, such as sulfuric acid, is used as the cleavage catalyst. Without intending to be bound by a particular theory, it is believed that this is because the liquid acid tends to have low solubility in cyclohexylbenzene, and the desired catalytic effect of the liquid acid can be significantly reduced as a result of high cyclohexylbenzene concentration. Experimental data have shown that partial removal of cyclohexylbenzene concentration from the oxidation product before it is fed to the cleavage step can significantly improve the selectivity of the cleavage reaction to form the desired products, i.e., cyclohexanone and/or phenol.

Because cyclohexylbenzene hydroperoxide is prone to decomposition at an elevated temperature, e.g., at above 150° C., the removal of cyclohexylbenzene from the oxidation product should generally be conducted at a relatively low temperature, e.g., no higher than 150° C., or no higher than 140° C., or no higher than 130° C., or no higher than 120° C., or even no higher than 110° C. Cyclohexylbenzene has a high boiling point (239° C. at 101 kPa). Thus, at the acceptable cyclohexylbenzene-removal temperature, cyclohexylbenzene tends to have very low vapor pressure. Accordingly, desirably, to effectively remove a meaningful amount of cyclohexylbenzene from the oxidation product, the oxidation product is subjected to a very low absolute pressure, e.g., in a range from Pc1 kPa to Pc2 kPa, where Pc1 and Pc2 can be, independently, 0.13, 0.15, 0.20, 0.25, 0.26, 0.30, 0.35, 0.39, 0.40, 0.45, 0.50, 0.60, 0.65, 0.70, 0.75, 0.80, 0.85, 0.90, 0.95, 1.00, 1.33, 1.50, 2.00, 2.50, 2.66, as long as Pc1<Pc2. Advantageously, Pc1=0.27, and Pc2=2.00.

Where cyclohexylbenzene is partly removed from the oxidation product before cleavage, water contained in the oxidation product can be at least partly removed at the same time and in the same vessel where the cyclohexylbenzene is partly removed at a low absolute internal pressure.

Because of the very low absolute pressure required for effective cyclohexylbenzene removal, it is highly desired that before the oxidation product is subjected to cyclohexylbenzene removal, components with boiling points substantially lower than cyclohexylbenzene, such as water, benzene, cyclohexane, lower acids, and the like, contained in the oxidation product are removed at a relatively high pressure before the mixture is subjected to the very low pressure required for cyclohexylbenzene removal, such that the vacuum pump used for imparting the very low pressure is not overwhelmed. To that end, the oxidation product, upon exiting the oxidation reactor, may be first flashed in a first vessel such as a flashing drum at an absolute pressure in a range from Pf1 kPa to Pf2 kPa, where Pf1 and Pf2 can be, independently, 2.67, 3.00, 3.50, 4.00, 4.50, 5.00, 6.00, 7.00, 8.00, 9.00, 10.00, 11.00, 12.00, 13.00, 13.33, 14.00, 15.00, 20.00, 25.00, 30.00, 35.00, 40.00, 45.00, 50.00, as long as Pf1<Pf2, where a majority of the water contained in the oxidation product is removed, and desirably less than AA % of the cyclohexylbenzene contained in the oxidation product is removed, the percentage based on the total amount of cyclohexylbenzene contained in the oxidation product, where AA can be: 5, 4, 3, 2, 1, 0.8, 0.6, 0.5, 0.4, 0.3, 0.2, or 0.1.

Removal of cyclohexylbenzene from the oxidation product can be advantageously conducted in a concentrator comprising one or more falling film evaporator(s), such as those descried in co-pending, co-assigned U.S. provisional patent application Ser. No. 61/841,072 filed on Jun. 28, 2013 and entitled "Process for Concentrating a Mixture Containing Organic Hydroperoxide." The concentrator advantageously employs one or more falling film evaporators operating in parallel and/or in series operating under very low absolute pressure(s) described above. Because cyclohexylbenzene has a lower boiling point than cyclohexylbenzene hydroperoxide, a portion of the cyclohexylbenzene contained in the oxidation product evaporates under the very low pressure and is enriched in the vapor phase, condensed and collected for recycling back to the oxidizing step. Since by-products produced in the oxidizing step tend to accumulate in the condensed cyclohexylbenzene stream, a washing or extracting treatment of the condensed cyclohexylbenzene using an aqueous dispersion or other agent may be desired before the recycling thereof to the oxidizing step in order to prevent interference of the oxidation reaction of cyclohexylbenzene by the accumulated oxidation by-products. Such aqueous dispersion may be acidic, basic, or neutral in pH. The washing or extracting treatment may advantageously include a first step of chemical wash followed by a step of washing using water only. The thus washed reclaimed cyclohexylbenzene may be dried by using a water sorbent, such as a 3 Å molecular sieve before being recycled to oxidizing step. Alternatively, because water up to a certain amount is tolerated in the oxidation reactor, the thus washed cyclohexylbenzene, which contains a significant amount of water, may be fed to the oxidizing step directly without drying as at least a portion of the total feed, thus eliminating the cost of drying.

As an alternative approach, water removal of the optionally treated oxidation product can be effected by passing the liquid mixture through a water sorbent, such as a 3 Å molecular sieve. Advantageously, the water sorbent also adsorbs the oxidation catalyst, which may be reclaimed by washing with a polar solvent.

Additionally or alternatively, after water removal and before or after partial cyclohexylbenzene removal, all or a portion of the oxidation product may be cooled to cause crystallization of the unreacted imide oxidation catalyst, which may then be separated either by filtration or by scraping from a heat exchanger surface used to effect the crystallization.

Cleavage Reaction

As discussed above, the process for making phenol and cyclohexanone from benzene includes cleaving at least a portion of the cyclohexylbenzene hydroperoxide contained in the oxidation product in the presence of an acid catalyst to produce a cleavage reaction mixture comprising the acid catalyst, phenol, and cyclohexanone. As used herein, "cleaving" means causing a cleavage reaction to occur. In the cleavage reaction, at least a portion of the desired cyclohexyl-1-phenyl-1-hydroperoxide desirably decomposes in high selectivity to cyclohexanone and phenol, and further, other hydroperoxides present may decompose to form various products, discussed below.

The acid catalyst may be at least partially soluble in the cleavage reaction mixture, stable at a temperature of at least 185° C. and has a lower volatility (higher normal boiling point) than cyclohexylbenzene.

Acid catalysts include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

As a result of potentially high amounts of cyclohexylbenzene in the cleavage reaction mixture, considerably higher than cumene in the Hock process material undergoing a cleavage reaction, it may be convenient in the present invention to use more acid catalyst to effect the cleavage reaction than typically believed optimal in the Hock process, to at least partially overcome the insolubility of the acid in the cleavage reaction mixture. However, lower amounts of acid catalyst may be applied in the present invention, with appropriate additional cleavage reactor volume and residence time of the cleavage reaction mixture in the cleavage reactor to obtain high hydroperoxide conversion.

The cleavage reaction occurs under cleavage conditions. Suitable cleavage conditions include a temperature of at least 20° C. and no greater than 200° C., or at least 40° C. and no greater than 120° C., and a pressure of at least 1 and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

The cleavage reaction mixture may contain the acid catalyst at a concentration in a range from Cac1 ppm to Cac2 ppm by weight of the total weight of the cleavage reaction mixture, where Cac1 and Cac2 can be, independently, 10, 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cac1<Cac2. Advantageously, Cac1 is 50, and Cac2 is 200.

Conversion of any hydroperoxide, such as cyclohexyl-1-phenyl-1-hydroperoxide, and conveniently all cyclohexyl-1-phenyl-1-hydroperoxide and other hydroperoxides, may be very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given specie of hydroperoxide, or of all cyclohexyl-1-phenyl-1-hydroperoxide, and other hydroperoxides present in the at least a portion of the oxidation product undergoing the cleavage reaction. This is desirable because any hydroperoxide, even the cyclohexyl-1-phenyl-1-hydroperoxide, becomes a contaminant in the cleavage reaction mixture and treated cleavage reaction mixture, discussed below. Hydroperoxides cause undesired chemistry when decomposed under uncontrolled conditions outside the cleavage reaction, or if thermally decomposed under the conditions in a distillation column.

The major products of the cleavage reaction of cyclohexyl-1-phenyl-1-hydroperoxide are phenol and cyclohexanone according to the following desired Reaction-12:

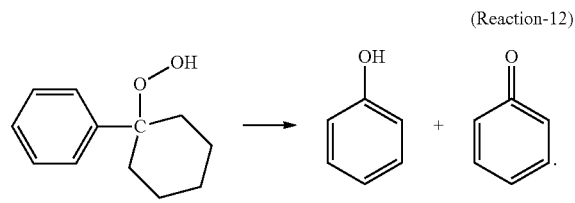

(Reaction-12)

Desirably, each mole of cyclohexyl-1-phenyl-1-hydroperoxide produces one mole of phenol and one mole of cyclohexanone. However, due to side reactions, the selectivity of the cleavage reaction of phenol can range from Sph1% to Sph2% and the selectivity of cyclohexanone can range from Sch1% to Sch2%, where Sph1, Sph2, Sch1, and Sch2 can be, independently, 85, 87, 88, 89, 90, 91, 92, 93, 94, 95, 96, 97, 98, 99, or even 99.5, as long as Sph1<Sph2, and Sch1<Sch2.

Besides the cleavage feed comprising cyclohexylbenzene hydroperoxide, cyclohexylbenzene and other components originating directly from the oxidation product, the cleavage reaction mixture may further comprise other added materials, such as the cleavage catalyst, a solvent, and one or more products of the cleavage reaction such as phenol and cyclohexanone recycled from the cleavage reaction effluent, or from a downstream separation step. Thus, the cleavage reaction mixture inside the cleavage reactor may comprise, based on the total weight of the cleavage reaction mixture: (i) phenol at a concentration from Cph1 wt % to Cph2 wt %, where Cph1 and Cph2 can be, independently, 20, 25, 30, 35, 40, 45, 50, 55, 60, 65, 70, 75, or 80, as long as Cph1<Cph2; (ii) cyclohexanone at a concentration from Cch1 wt % to Cch2 wt %, where Cch1 and Cch2 can be, independently, 20, 25, 30, 35, 40, 45, 50, 55, 60, 65, 70, 75, or 80, as long as Cch1<Cch2; (iii) cyclohexylbenzene at a concentration from Cchb1 wt % to Cchb2 wt %, where Cchb1 and Cchb2 can be, independently, 5, 8, 9, 10, 12, 14, 15, 18, 20, 22, 24, 25, 26, 28, 30, 35, 40, 45, 50, 55, 60, 65, 70, as long as Cchb1<Cchb2.

As used herein, a "contaminant" or a "contaminant byproduct" may include any unwanted hydrocarbon or oxygenated hydrocarbon component in the cleavage reaction mixture or the neutralized cleavage mixture, or any portion of either; that is anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage reaction mixture, or the neutralized cleavage mixture, or any portion thereof may have been produced in any element of the present invention, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation product from (ii).

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. Alternatively, the cleavage reactor comprises a plurality of reactors in series, each performing a portion of the conversion reaction, optionally operating in different modes and at different conditions selected to enhance the cleavage reaction at the pertinent conversion range. For example, the cleavage reactor can be a catalytic distillation unit.

The cleavage reactor may be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) remove any heat generated.

The cleavage reaction product exiting cleavage reactor may comprise, based on the total weight of the cleavage reaction mixture: (i) phenol at a concentration from Cph3 wt % to Cph4 wt %, where Cph1 and Cph2 can be, independently, 20, 25, 30, 35, 40, 45, 50, 55, 60, 65, 70, 75, or 80, as long as Cph3<Cph4; (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; (iii) cyclohexylbenzene at a concentration from Cchb3 wt % to Cchb4 wt %, where Cchb3 and Cchb4 can be, independently, 5, 8, 9, 10, 12, 14, 15, 18, 20, 22, 24, 25, 26, 28, 30, 35, 40, 45, 50, 55, 60, 65, 70, as long as Cchb3<Cchb4.

At least a portion of the cleavage reaction mixture may be subjected to a neutralization reaction, which may include all or some fraction of the cleavage reaction mixture as directly produced without undergoing any separation (e.g., some fraction resulting from diverting some amount of the cleavage reaction mixture as directly produced to another disposition, such as temporary storage). Thus, the at least a portion of the cleavage reaction mixture may have the same composition as the cleavage reaction mixture. Further, all or some of the cleavage reaction mixture as directly produced may undergo one or more separations, and an appropriate product of that separation (or separations), now modified in composition relative the cleavage reaction mixture as directly produced, may provide the at least a portion of the cleavage reaction mixture subjected to the neutralization reaction.

The cyclohexylbenzene contained in the cleavage reaction product can be separated from other major components, such as phenol and cyclohexanone by, e.g., distillation. The separated cyclohexylbenzene can then be treated and/or purified, e.g., by washing using an aqueous dispersion, before delivered to step along with cyclohexylbenzene supplied from other resources, such as fresh cyclohexylbenzene produced the hydroalkylation reactor and a recycle cyclohexylbenzene stream from the cyclohexylbenzene hydroperoxide concentrator.

Contaminant Treatment

As discussed above, the cleavage reaction mixture may comprise one or more contaminants. The processes may further comprise contacting at least a portion of a contaminant with an acidic material to convert at least a portion of the contaminant to a converted contaminant, thereby producing a modified reaction mixture. Detailed description of the contaminant treatment process can be found, e.g., in International Publication WO2012/036822A1, the relevant content of which is incorporated herein by reference in its entirety.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

Non-limiting embodiments of the processes of the present disclosure include:

E1. A hydroalkylation process, the process comprising:

(I) supplying hydrogen gas and an aromatic compound into a hydroalkylation reactor;

(II) contacting the hydrogen and the aromatic compound with a hydroalkylation catalyst comprising a first hydrogenation metal component and an alkylation component in a first reaction zone in the hydroalkylation reactor to obtain a first reaction mixture comprising hydrogen, an alkylated aromatic compound and an olefin; and (III) contacting the first reaction mixture with a hydrogenation catalyst comprising a second hydrogenation metal component and essentially free of an alkylation component in a second reaction zone in the hydroalkylation reactor to obtain a second reaction mixture.

E2. The hydroalkylation process of E1, wherein the aromatic compound is represented by the following general formula (F-I):

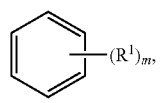
(F-I)

where:
$R^1$, the same or different at each occurrence, each independently represents a substituted or unsubstituted linear, branched acyclic, or cyclic alkyl or alkenyl group having from 1 to 20 carbon atoms; and
m is an integer from 0 to 5.

E3. The hydroalkylation process of E2, wherein the aromatic compound is selected from benzene, toluene, o-xylene, m-xylene, p-xylene, ethylbenzene, methylethylbenzene, and mixtures of at least two thereof.

E4. The hydroalkylation process of E2, wherein the alkylated aromatic compound is represented by the following general formula (F-II):

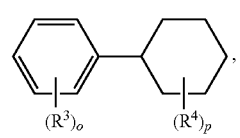
(F-II)

where:
$R^3$ and $R^4$, the same or different at each occurrence, each independently represents a substituted or unsubstituted linear, branched acyclic, or cyclic alkyl or alkenyl having from 1 to 20 carbon atoms; and
o and p are independently integers from 0 to 5.

E5. The hydroalkylation process of E4, wherein the alkylated aromatic compound is selected from:
cyclohexylbenzene;
dicyclohexylbenzene;
tricyclohexylbenzene;
methylcyclohexyltoluene;
methylcyclohexyl-ethylbenzene;
ethylcyclohexyl-ethylbenzene;
propylcyclohexyl-propylbenzene;
butylcyclohexyl-butylbenzene;
dimethylcyclohexyl-dimethylbenzene;
diethylcyclohexyl-diethylbenzene;
trimethylcyclohexyl-trimethylbenzene;
isopropylcyclohexylcumene;
methylethylcyclohexyl-methylethylbenzene; and
combinations and mixtures of at least two thereof.

E6. The hydroalkylation process of any of E1 to E5, wherein the first reaction mixture has a concentration of one or more olefin of C1 wt %, the second reaction mixture has a concentration of phenylcyclohexene of C2 wt %, and C1/C2≥2.0.

E7. The hydroalkylation process of E6, wherein the one or more olefin is represented by the following general formula (F-III), (F-IV) and/or (F-V):

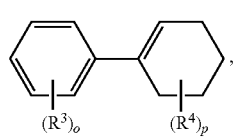
(F-III)

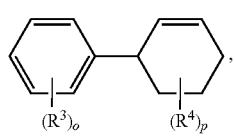
(F-IV)

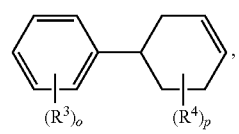
(F-V)

where $R^3$, $R^4$, o, and p have the same meaning as in formula (F-II).

E8. The hydroalkylation process of E1, wherein the aromatic compound is benzene, the alkylated aromatic compound is cyclohexylbenzene, and the olefin is phenylcyclohexene.

E9. The hydroalkylation process of E8, wherein the first reaction mixture has a concentration of phenylcyclohexene of C1 wt %, the second reaction mixture has a concentration of phenylcyclohexene of C2 wt %, and C1/C2≥R1, where R1 can be 2.0, 2.5, 3.0, 3.5, 4.0, 4.5, 5.0, 6.0, 7.0, 8.0, 9.0, or 10.0.

E10. The hydroalkylation process of E1 to E8, wherein the concentration of the olefin in the first reaction mixture is at least 50 ppm by weight, and the concentration of the olefin in the second reaction mixture is at most 25 ppm by weight.

E11. The hydroalkylation process of any of E1 to E10, wherein the first hydrogenation metal component comprises at least one of Re, Ru, Os, Rh, Ir, Ni, Pd, and Pt, the alkylation component comprises a solid acid, and the second hydrogenation metal component comprises at least one of Re, Ru, Os, Rh, Ir, Ni, Pd, and Pt.

E12. The hydroalkylation process of any of E1 to E11, wherein the hydroalkylation catalyst comprises a first inorganic oxide support component, and the hydrogenation catalyst comprises a second inorganic oxide support.

E13. The hydroalkylation process of E12, wherein the first inorganic oxide support component comprises at least one of alumina, silica, zirconia, titania, and the second inorganic oxide support comprises at least one of alumina, silica, zirconia, titania.

E14. The hydroalkylation process of E13, wherein the solid acid comprises a molecular sieve in the MCM-22 family.

E15. The hydroalkylation process of any of E1 to E14, wherein the hydrogenation catalyst comprises Pt, and at least one of alumina and silica.

E16. The hydroalkylation process of any of E1 to E15, wherein the alkylation component constitutes from AC1 wt % to AC2 wt % of the total weight of the hydroalkylation catalyst, where AC1 and AC2 can be, independently, 10, 15, 20, 25, 30, 35, 40, 45, 50, 55, 60, 65, 70, 75, and 80, as long as AC1<AC2.

E17. The hydroalkylation process of any of E1 to E16, wherein the hydroalkylation catalyst comprises a first inorganic oxide support component, and the second inorganic oxide support constitutes from BC1 wt % to BC2 wt % of the total weight of the hydroalkylation catalyst, where BC1 and BC2 can be, independently, 10, 15, 20, 25, 30, 35, 40, 45, 50, 55, 60, 65, 70, 75, 80, as long as BC1<BC2.

E18. The hydroalkylation process of any of E1 to E17, wherein the first hydrogenation metal, expressed in terms of metal only, constitutes from MC1 wt % to MC2 wt % of the total weight of the hydroalkylation catalyst, where MC1 and MC2 can be, independently, 0.01, 0.15, 0.20, 0.25, 0.30, 0.35, 0.40, 0.45, 0.50, 0.60, 0.70, 0.80, 0.90, 1.00, 2.00, 3.00, 4.00, 5.00, 6.00, 7.00, 8.00, 9.00, or 10.00, as long as MC1<MC2.

E19. The hydroalkylation process of any of E1 to E18, wherein the contacting step (II) is conducted at a temperature in a range from TA1° C. to TA2° C., and an absolute pressure in a range from 100 kPa to 5000 kPa, where TA1 and TA2 can be, independently, 80, 90, 100, 110, 120, 130, 140, 150, 160, 170, or 180, as long as TA1<TA2, and PA1 and PA2 can be, independently, 100, 200, 300, 400, 500, 600, 700, 800, 900, 1000, 1500, 2000, 2500, 3000, 3500, 4000, 4500, or 5000, as long as PA1<PA2.

E20. The hydroalkylation process of any of E1 to E19, wherein during the contacting step (II), at least part of the aromatic compound is in liquid phase.

E21. The hydroalkylation process of any of E1 to E20, wherein the contacting step (II) is conducted at a space velocity (WHSV) of SV1 to SV2 gram of aromatic compound per gram of hydroalkylation catalyst per hour, where SV1 and SV2 can be, independently, 0.5, 1.0, 1.5, 2.0, 2.5, 3.0, 3.5, 4.0, 5.0, 6.0, 7.0, 8.0, 9.0, 10.0, 11.0, 12.0, 13.0, 14.0, or 15.0, as long as SV1<SV2.

E22. The hydroalkylation process of any of E1 to E21, wherein in the supplying step (I), the molar ratio of the hydrogen to the aromatic compound is in a range from MR1 to MR2, wherein MR1 and MR2 can be, independently, 0.01, 0.02, 0.03, 0.05, 0.08, 0.10, 0.20, 0.30, 0.40, 0.50, 0.60, 0.70, 0.90, 1.00, 2.00, 3.00, 4.00, 5.00, 6.00, 7.00, 8.00, 9.00, 10.00, 20.00, 30.00, 40.00, 50.00, 60.00, 70.00, 80.00, 90.00, or 100, as long as MR1<MR2.

E23. A process for making phenol and/or cyclohexanone, the process comprising:
(A) producing cyclohexylbenzene by a process of any of E1 to E22:
(I) supplying hydrogen and benzene into a hydroalkylation reactor;
(II) contacting the hydrogen and benzene with a hydroalkylation catalyst comprising a first hydrogenation metal component and an alkylation component in a first reaction zone in the reactor to obtain a first reaction mixture comprising hydrogen, cyclohexylbenzene and phenylcyclohexene; and
(III) contacting the first reaction mixture with a hydrogenation catalyst comprising a second hydrogenation metal component and essentially free of an alkylation component in a second reaction zone in the hydroalkylation reactor to obtain a second reaction mixture comprising cyclohexylbenzene;
(B) oxidizing at least a portion of the cyclohexylbenzene in the second reaction mixture to obtain an oxidation product comprising cyclohexylbenzene hydroperoxide; and
(C) subjecting at least a portion of the cyclohexylbenzene hydroperoxide in the oxidation product to cleavage to obtain a cleavage product comprising phenol and cyclohexanone.

E24. A hydroalkylation reactor comprising a vessel comprising:
at least one upper port through which $H_2$ and an aromatic compound can be fed into the vessel;
a bed of a hydroalkylation catalyst in proximity to but below the at least one upper port comprising a first hydrogenation metal component and an alkylation component in a first reaction zone;
a bed of a hydrogenation catalyst comprising a second hydrogenation metal component and essentially free of an alkylation component in a second reaction zone below the first reaction zone; and
at least one lower port below the bed of the hydrogenation catalyst through which the hydroalkylation effluent can exit the reactor.

E25. The hydroalkylation reactor of E24, wherein the first hydrogenation metal component comprises at least one of Pd, Pt, Ni, Rh, Ir, Ru, and Os, the alkylation component comprises a solid acid, and the second hydrogenation metal component comprises at least one of Pd, Pt, Ni, Rh, Ir, Ru, and Os.

E26. The hydroalkylation reactor of E24 or E25, wherein the hydroalkylation catalyst comprises a first inorganic oxide support component, and the hydrogenation catalyst comprises a second inorganic oxide support.

E27. The hydroalkylation reactor of any of E24 to E26, wherein the first inorganic oxide support component comprises at least one of alumina, silica, zirconia, titania, and the second inorganic oxide support comprises at least one of alumina and silica.

E28. The hydroalkylation reactor of any of E24 to E27, wherein the reactor comprises at least one lower port through which a stream comprising $H_2$ exits, and at least one lower port through a stream of liquid substantially free of $H_2$ exits.

The invention claimed is:

1. A hydroalkylation process, the process comprising:
   (I) supplying hydrogen and an aromatic compound into a hydroalkylation reactor;
   (II) contacting the hydrogen and the aromatic compound with a hydroalkylation catalyst comprising a first hydrogenation metal component and an alkylation component in a first reaction zone in the hydroalkylation reactor to obtain a first reaction mixture comprising hydrogen, an alkylated aromatic compound and an olefin; and
   (III) contacting the first reaction mixture with a hydrogenation catalyst comprising a second hydrogenation metal component and essentially free of an alkylation component in a second reaction zone in the hydroalkylation reactor to obtain a second reaction mixture.

2. The hydroalkylation process of claim 1, wherein the aromatic compound is selected from benzene, toluene, o-xylene, m-xylene, p-xylene, ethylbenzene, methylethylbenzene, and mixtures of at least two thereof.

3. The hydroalkylation process of claim 1, wherein the aromatic compound is benzene, the alkylated aromatic compound is cyclohexylbenzene, and the olefin is phenylcyclohexene.

4. The hydroalkylation process of claim 3, wherein the first reaction mixture has a concentration of phenylcyclohexene of C1 wt %, the second reaction mixture has a concentration of phenylcyclohexene of C2 wt %, and C1/C2≥2.0.

5. The hydroalkylation process of claim 1, wherein the concentration of the olefin in the first reaction mixture is at least 50 ppm by weight, and the concentration of the olefin in the second reaction mixture is at most 25 ppm by weight.

6. The hydroalkylation process of claim 1, wherein the first hydrogenation metal component comprises at least one of Re, Ru, Os, Rh, Ir, Ni, Pd, and Pt, the alkylation component comprises a solid acid, and the second hydrogenation metal component comprises at least one of Re, Ru, Os, Rh, Ir, Ni, Pd, and Pt.

7. The hydroalkylation process of claim 1, wherein the hydroalkylation catalyst comprises a first inorganic oxide support component, and the hydrogenation catalyst comprises a second inorganic oxide support.

8. The hydroalkylation process of claim 7, wherein the first inorganic oxide support component comprises at least one of alumina, silica, zirconia, titania, and the second inorganic oxide support comprises at least one of alumina, silica, zirconia, titania.

9. The hydroalkylation process of claim 6, wherein the solid acid comprises a molecular sieve in the MCM-22 family.

10. The hydroalkylation process of claim 1, wherein the hydrogenation catalyst comprises Pt and at least one of alumina and silica.

11. The hydroalkylation process of claim 1, wherein the contacting step (II) is conducted at a temperature in a range from 90° C. to 180° C., and a pressure in a range from 100 kPa to 5000 kPa.

12. The hydroalkylation process of claim 11, wherein during the contacting step (II), at least part of the aromatic compound is in liquid phase.

13. The hydroalkylation process of claim 1, wherein the contacting step (II) is conducted at a space velocity of 0.5 to 15 g aromatic compound/(g catalyst hour) WHSV.

14. The hydroalkylation process of claim 1, wherein in the supplying step (I), the molar ratio of the hydrogen to the aromatic compound is in a range from 0.01 to 100.

15. A process for making phenol and/or cyclohexanone, the process comprising:
   (A) producing cyclohexylbenzene by:
      (I) supplying hydrogen and benzene into a hydroalkylation reactor;
      (II) contacting the hydrogen and benzene with a hydroalkylation catalyst comprising a first hydrogenation metal component and an alkylation component in a first reaction zone in the reactor to obtain a first reaction mixture comprising hydrogen, cyclohexylbenzene and phenylcyclohexene; and
      (III) contacting the first reaction mixture with a hydrogenation catalyst comprising a second hydrogenation metal component and essentially free of an alkylation component in a second reaction zone in the hydroalkylation reactor to obtain a second reaction mixture comprising cyclohexylbenzene;
   (B) oxidizing at least a portion of the cyclohexylbenzene in the second reaction mixture to obtain an oxidation product comprising cyclohexylbenzene hydroperoxide; and
   (C) subjecting at least a portion of the cyclohexylbenzene hydroperoxide in the oxidation product to cleavage to obtain a cleavage product comprising phenol and cyclohexanone.

16. The process of claim 15, wherein the first reaction mixture has a concentration of phenylcyclohexene of C1 wt %, the second reaction mixture has a concentration of phenylcyclohexene of C2 wt %, and C1/C2≥2.0.

17. The hydroalkylation process of claim 15, wherein the concentration of the olefin in the first reaction mixture is at least 50 ppm by weight, and the concentration of phenylcyclohexene in the second reaction mixture is at most 25 ppm by weight.

18. The hydroalkylation process of claim 15, wherein the first hydrogenation metal component comprises at least one of Pd, Pt, Ni, Rh, Ir, Ru, and Os, the alkylation component comprises a solid acid, and the second hydrogenation metal component comprises at least one of Pd, Pt, Ni, Rh, Ir, Ru, and Os.

19. The hydroalkylation process of claim 15, wherein the hydroalkylation catalyst comprises a first inorganic oxide support component, and the hydrogenation catalyst comprises a second inorganic oxide support.

20. The hydroalkylation process of claim 19, wherein the first inorganic oxide support component comprises at least one of alumina, silica, zirconia, titania, and the second inorganic oxide support comprises at least one of alumina and silica.

21. A hydroalkylation reactor comprising a vessel comprising:
   at least one upper port through which $H_2$ and an aromatic compound can be fed into the vessel;
   a bed of a hydroalkylation catalyst in proximity to but below the at least one upper port comprising a first hydrogenation metal component and an alkylation component in a first reaction zone;
   a bed of a hydrogenation catalyst comprising a second hydrogenation metal component and essentially free of an alkylation component in a second reaction zone below the first reaction zone; and
   at least one lower port below the bed of the hydrogenation catalyst through which the hydroalkylation effluent can exit the reactor.

22. The hydroalkylation reactor of claim 21, wherein wherein the first hydrogenation metal component comprises at least one of Pd, Pt, Ni, Rh, Ir, Ru, and Os, the alkylation component comprises a solid acid, and the second hydrogenation metal component comprises at least one of Pd, Pt, Ni, Rh, Ir, Ru, and Os.

23. The hydroalkylation reactor of claim 21, wherein the hydroalkylation catalyst comprises a first inorganic oxide support component, and the hydrogenation catalyst comprises a second inorganic oxide support.

24. The hydroalkylation reactor of claim 21, wherein the first inorganic oxide support component comprises at least one of alumina, silica, zirconia, titania, and the second inorganic oxide support comprises at least one of alumina and silica.

* * * * *

UNITED STATES PATENT AND TRADEMARK OFFICE
CERTIFICATE OF CORRECTION

| | | |
|---|---|---|
| PATENT NO. | : 9,169,170 B2 | Page 1 of 1 |
| APPLICATION NO. | : 14/477243 | |
| DATED | : October 27, 2015 | |
| INVENTOR(S) | : Gabor Kiss et al. | |

It is certified that error appears in the above-identified patent and that said Letters Patent is hereby corrected as shown below:

On the title page of the patent, in item 60, Related U.S. Application Data, please delete "Provisional application No. 61/885,336, filed on Jan. 16, 2014" and insert --Provisional application No. 61/885,336, filed on October 1, 2013.--

Signed and Sealed this
Seventeenth Day of May, 2016

Michelle K. Lee
*Director of the United States Patent and Trademark Office*